United States Patent [19]

Mercier

[11] Patent Number: 4,957,506
[45] Date of Patent: Sep. 18, 1990

[54] OPTICAL SYSTEM USING AN OPHTHALMIC LENS AND AN INTRA-OCULAR LENS TO IMPROVE THE SIGHT OF A PERSON SUFFERING FROM MACULAR DEGENERATION

[75] Inventor: Jean-Louis Mercier, Fontenay Les Briis, France

[73] Assignee: Essilor International Cie Generale d'Optique, Fontenay Les Briis, France

[21] Appl. No.: 400,871

[22] Filed: Aug. 30, 1989

[30] Foreign Application Priority Data

Sep. 6, 1988 [FR] France .................... 88 11623

[51] Int. Cl.⁵ .............................. A61F 2/16
[52] U.S. Cl. ........................................ 623/6
[58] Field of Search ............................ 623/6

[56] References Cited

U.S. PATENT DOCUMENTS

| | | | |
|---|---|---|---|
| 4,504,982 | 3/1985 | Burk | 623/6 |
| 4,666,446 | 5/1987 | Koziol | 623/6 |
| 4,710,193 | 12/1987 | Volk | 623/6 |

FOREIGN PATENT DOCUMENTS

| | | |
|---|---|---|
| 0157476 | 10/1985 | European Pat. Off. . |
| 0162573 | 11/1985 | European Pat. Off. . |
| 0195881 | 10/1986 | European Pat. Off. . |
| 0242043 | 10/1987 | European Pat. Off. . |
| 1089254 | 3/1955 | France . |
| 2509482 | 1/1983 | France . |
| WO83/01566 | 5/1983 | PCT Int'l Appl. ............ 623/6 |
| WO83/03481 | 10/1983 | PCT Int'l Appl. . |
| 20620 | of 1910 | United Kingdom . |

Primary Examiner—Ronald Frinks
Attorney, Agent, or Firm—Charles E. Brown; Charles A. Brown

[57] ABSTRACT

An optical system for improving the sight of a person suffering from macular degeneration comprises a high positive power ophthalmic lens adapted to be disposed in front of the eye to be treated and a high negative power intra-ocular lens adapted to be implanted in the eye to be treated after removal of its crystalline lens. At least one surface of each lens is an aspherical surface of revolution. This aspherical surface of revolution preferably has a generatrix that is a conic section.

8 Claims, 2 Drawing Sheets

4a

4b

4c

5b

5c

4'a

4'd

4'e

4'f

5'd

5'e

5'f

OPTICAL SYSTEM USING AN OPHTHALMIC LENS AND AN INTRA-OCULAR LENS TO IMPROVE THE SIGHT OF A PERSON SUFFERING FROM MACULAR DEGENERATION

BACKGROUND OF THE INVENTION

1. Field of the invention

The present invention builds on the work of Georges BAIKOFF, Bernard GARNIER and Yves MAIGRET, and is generally concerned with improving the sight of a person suffering from macular degeneration, that is to say degeneration of the macula lutea of the retina of one or both eyes.

2. Description of the prior art

In macular degeneration, which usually affects only persons aged more than 65 years, there is a drop in the activity of the rods in the area of the retina concerned and this has two results; where near sight is concerned it becomes impossible to read and where far sight is concerned the loss of clear vision makes walking difficult.

In brief, the result is some form of visual impairment.

A first proposal for improving the sight of persons suffering from macular degeneration was to place before the eye to be treated, rather than a single ophthalmic lens, an optical system comprising a plurality of such lenses, constituting a Galilean telescope, for example, adapted to magnify the image formed on the retina of the eye concerned and so to illuminate a maximum number of the rods thereof.

However, the image enlargement feasible with any such optical system is relatively moderate and, more importantly, although some degree of vision can be restored in this way this applies only to a limited field, minimizing the benefit of this solution.

In this type of optical system all the lenses remain external to the eye.

Furthermore, optical systems of this kind using a Galilean telescope system are heavy and bulky.

More recently there has been proposed an optical system using the eye itself.

Formulated in various ways, an optical system of this kind generally comprises a combination of two lenses, namely a high positive power ophthalmic lens placed before the eye to be treated and a high negative power intra-ocular lens implanted in the eye in place of its crystalline lens.

The intra-ocular lens may be implanted in the posterior chamber of the eye, for example.

Alternatively, it may be planted in the anterior chamber of the eye.

In either case, the image magnification achieved with an optical system of this kind can be very much greater than that obtained with an optical system external to the eye and the corresponding field may also and advantageously be larger.

However, although consideration has been given to forming one of the lenses constituting this optical system, in practise the ophthalmic lens disposed before the eye, with an aspherical surface of revolution, there usually remain non-negligible aberrations in such optical systems, especially when the intra-ocular lens is implanted in the anterior chamber of the eye, both to facilitate the surgery required and to enable further intervention at a later stage. The inevitable result of this is some degradation of the quality of the image obtained.

The present invention is based on the observation that it is possible to improve very significantly the quality of the image by providing an aspherical surface of revolution on both the lenses constituting an optical system of this kind.

SUMMARY OF THE INVENTION

The present invention consists in a system for improving the sight of a person suffering from macular degeneration comprising a high positive power ophthalmic lens adapted to be disposed in front of the eye to be treated and a high negative power intra-ocular lens adapted to be implanted in the eye to be treated after removal of its crystalline lens, wherein at least one surface of each lens is an aspherical surface of revolution.

The aspherical surface of revolution is preferably a surface of revolution for which the generatrix is a conic section.

By appropriately choosing the conic constant for both the surfaces concerned it is advantageously possible to implement an optical system for producing on the retina of the eye images corrected for coma and for longitudinal spherical aberration; for example, the longitudinal spherical aberration of the system that the optical system forms with the eye can be less than that of an emmetropic eye under the same conditions.

In more precise terms, it is advantageously possible to implement in accordance with the invention an optical system which for an object field of defined extent, in the order of $2 \times 10$ mm diameter, for example, is advantageously substantially aplanatic, the image of an object situated in a plane being formed exactly on the retina, itself likened to a plane, with no coma or longitudinal spherical aberration and which produces very little coma and very little astigmatism for larger fields.

Thus for a field of less than $2 \times 10$ mm this optical system is adapted to form for a point source a spot with a diameter in the order of five microns, which corresponds to the diameter of the retinal detectors and therefore guarantees a good quality image.

Also, as the resulting image field is in practise larger than the fovea and it is at the center of the fovea that the image of the point of fixation is formed with the gaze is fixed on an object, it is advantageously possible with the optical system in accordance with the invention to obtain good image quality for all the area (or central area) of vision which corresponds to the fovea and on which the accuracy of perception depends.

In brief, it is advantageously possible with the optical system in accordance with the invention to obtain on the retina of the eye concerned "clear" (that is virtually aberration-free) images.

The characteristics and advantages of the invention will emerge from the following description given by way of non-limiting example only with reference to the appended diagrammatic drawings.

BRIEF DESCRIPTION OF THE DRAWINGS

FIG. 4' is a set of diagrams to a different scale than FIG. 4, the first of which corresponds to the first diagram from FIG. 4 and the others of which complement the diagrams in FIG. 4.

FIG. 5' is a set of diagrams to the same scale as FIG. 4' complementing the diagrams of FIG. 5.

DESCRIPTION OF THE PREFERRED EMBODIMENT

Figure 1:
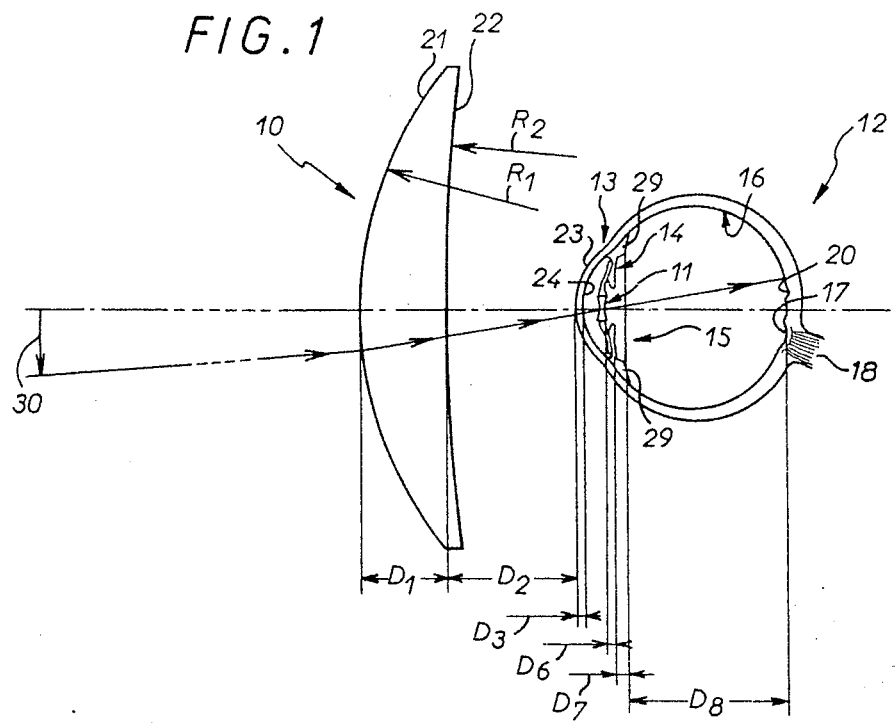
FIG. 1 is a view in elevation and cross-section of an optical system in accordance with the invention.

As shown in FIG. 1, the optical system in accordance with the invention which is designed to improve the sight of a person suffering from macular degeneration comprises a high positive power ophthalmic lens 10 disposed before the eye 12 to be treated and a high negative power intra-ocular lens 11 implanted in the eye 12 after removal of its crystalline lens.

FIG. 1 shows the cornea 13 of the eye 12, the iris 14, the sac 15 which previously contained the crystalline lens, the retina 16, the papilla 17 at the intra-ocular end of the optic nerve 18 and the fovea 20.

The front surface 21 of the ophthalmic lens 10 is convex.

Assuming for the moment that the front surface 21 is spherical, let $R_1$ be its radius.

The rear surface 22 of the ophthalmic lens 10 is substantially plane, being in fact very slightly concave.

It is a spherical surface.

Let $R_2$ be its radius.

Let $D_1$ be the distance between the corresponding optical surfaces along the axis of the system.

Finally, let $n_1$ be the refractive index of the material of the ophthalmic lens 10.

It will be assumed hereinafter that the ophthalmic lens 10 is at a distance $D_2$ from the cornea 13.

Let $R_3$ be the radius of the anterior surface 23 of the cornea 13, $R_4$ the radius of its posterior surface 24, $D_3$ the distance between the two surfaces 23 and 24 along the axis of the system and $n_3$ the refractive index between the latter.

In the preferred embodiment shown the intra-ocular lens 11 is implanted in the anterior chamber of the eye 12, that is to say in the part of the eye between the cornea 13 and the iris 14.

Let $D_4$ be the axial distance between the cornea 13 and the intra-ocular lens 11 and let $n_4$ be the refractive index of the corresponding aqueous humour.

Figure 2:
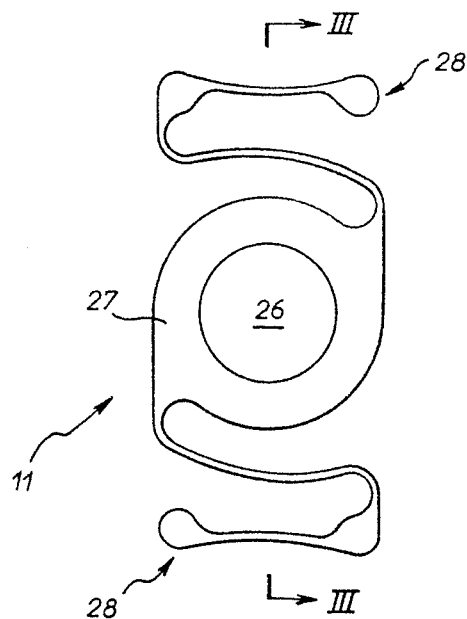
FIG. 2 is a plan view to a larger scale of an intra-ocular lens included in this optical system.
Figure 3:
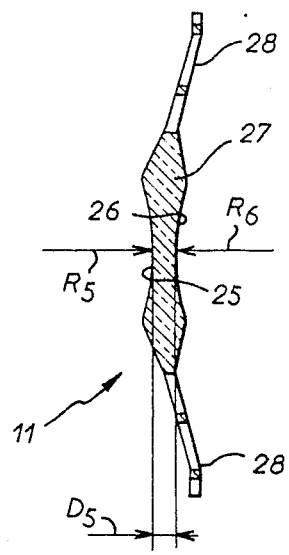
FIG. 3 is a view of this intra-ocular lens in axial cross-section on the line III—III in FIG. 2.

The intra-ocular lens 11 is a biconcave lens as shown in FIGS. 2 and 3.

Like the ophthalmic lens 10, it may be made from polymethyl methacrylate.

Let $R_5$ be the radius of its front surface 25, assuming for the moment that this front surface 25 is spherical, $R_6$ the radius of its rear surface 26, $D_5$ the distance between the two surfaces 25 and 26 along the axis of the system and $n_5$ the refractive index of the material.

In the known way the intra-ocular lens 11 comprises a thicker annulus 27 around its surfaces 25 and 26 and issuing from this at diametrally opposed positions two elastically deformable S-shape arms 28 adapted to bear on the ciliary bodies 29 of the eye 12, at the root of the iris 14.

The active part of the intra-ocular lens 11, formed by surfaces 25 and 26, has a relatively small diameter, in the order of 3 mm, for example.

Let $D_6$ be the axial distance between the intra-ocular lens 11 and the iris 14, $D_7$ the axial distance between the sac 15 and the iris 14 and $D_8$ the axial distance between the retina 17 and the sac 15.

Finally, let $n_5$ be the refractive index of the vitreous humour between the sac 15 and the retina 17 and $R_7$ the radius of the retina 17.

In accordance with the invention at least one of the surfaces of both the lenses 10 and 11 is an aspherical surface of revolution.

The generatrix of this aspherical surface of revolution is preferably a conic section, and this applies to both the lenses 10 and 11 concerned.

The surface of the lens which is an aspherical surface of revolution is preferably the front surface.

This is therefore the surface 21 in the case of the ophthalmic lens 10 and the surface 25 in the case of the intra-ocular lens 11.

The equation for an aspherical surface of revolution having a conic section generatrix may be written as follows:

$$Z = \frac{\frac{r^2}{R}}{1 + \sqrt{1 - (1 + K)\frac{r^2}{R^2}}}$$

In this equation:

Z is the coordinate along the axis of the system,
$r^2 = X^2 + Y^2$ where X and Y are coordinates in a plane perpendicular to the axis,
R is the osculatory radius of the surface at the center,
K is the conic constant enabling the surface with a required conic section generatrix to be deduced from a basic spherical surface of radius R.

In accordance with the invention the equation for the front surface 21 of the opthalmic lens 10 is therefore:

$$Z = \frac{\frac{r^2}{R_1}}{1 + \sqrt{1 - (1 + K_1)\frac{r^2}{R_1^2}}}$$

and the equation for the front surface 25 of the intra-ocular lens 11 is:

$$Z = \frac{\frac{r^2}{R_5}}{1 + \sqrt{1 - (1 + K_5)\frac{r^2}{R_5^2}}}$$

The images formed on the retina 16 are of good quality when, by appropriately using the conic constant, the generatrix of the aspherical surface of the ophthalmic lens 10 and that of the intra-ocular lens 11 is an ellipse.

For an optical system in which the intra-ocular lens 11 has an overall power of −50 diopters and for near sight, that is to say for viewing an object 30 assumed to be approximately 33.3 cm from the eye 12 concerned, good results are achieved when the conic constant $K_1$ of the ophthalmic lens 10 is between −0.1 and −0.3 for a refractive index $n_1$ of 1.523 and when the conic constant $K_5$ of the intra-ocular lens 11 is conjointly between $-2$ and $-4$ for a refractive index $n_5$ of 1.492.

Particulary satisfactory results are obtained when the conic constant $K_1$ for the ophthalmic lens 10 is $-0.185790$ and the conic constant $K_5$ for the intra-ocular lens 11 is conjointly equal to $-2.699500$.

Of course, the values of the conic constants $K_1$ and $K_5$ are directly related to the values of the refractive indexes $n_1$, $n_5$ of the lenses 10 and 11 concerned.

Thus there will be associated with another pair of values of the refractive indexes ($n_1$, $n_5$) another pair of values of the conic constants ($K_1$, $K_5$).

The table below summarizes numerical values for an optical system in accordance with the invention where the intra-ocular lens 11 has an overall power equal to $-50$ diopters for an object distance of 33.3 cm, showing that for the corresponding calculations it has been assumed that the anterior surface 23 of the cornea 13 is also an aspherical surface of revolution with an ellipse as the generatrix, with a conic constant $K_2$ equal to $-0.26000$.

Figure 4:
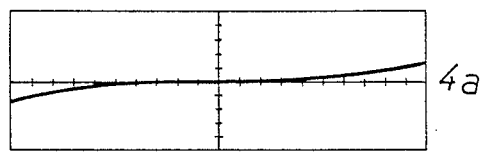
FIG. 4 is a set of diagrams showing the results obtained in a tangential plane with the optical system in accordance with the invention.
Figure 4:
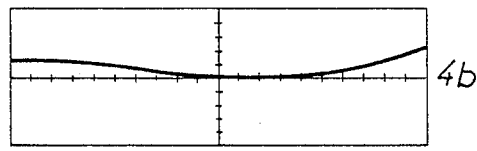
Figure 4:
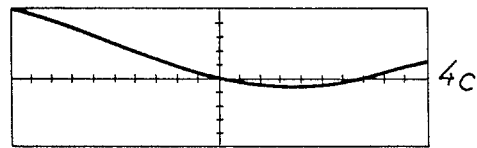

FIGS. 4, 4', 5 and 5' show the particularly satisfactory results achieved with an optical system of this kind.

They represent the transverse aberration in the image plane for a light beam from a point source at a distance of 33.3 cm.

For FIGS. 4 and 4' the light beam is in the tangential plane, in practise the plane of the figure.

Figure 5:
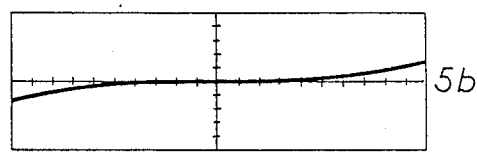
FIG. 5 is a set of diagrams showing to the same scale as FIG. 4 the results obtained in a sagittal plane with this optical system.
Figure 5:
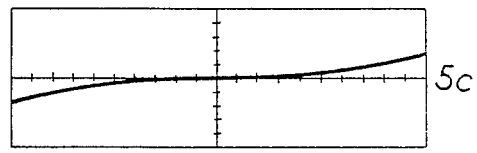
Figure 4:
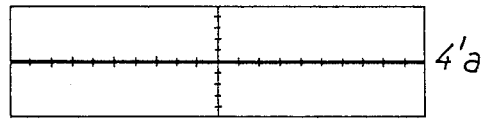
Figure 4:
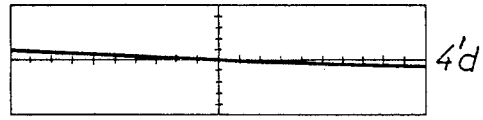
Figure 4:
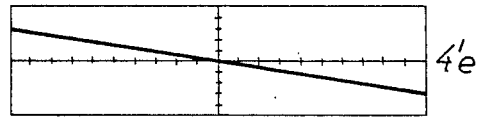
Figure 4:
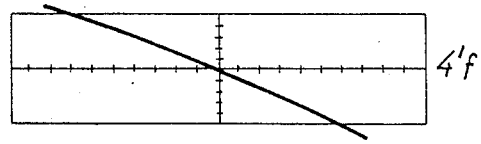
Figure 5:
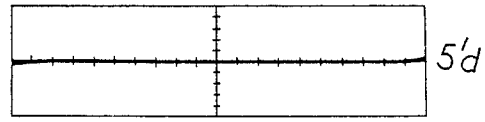
Figure 5:
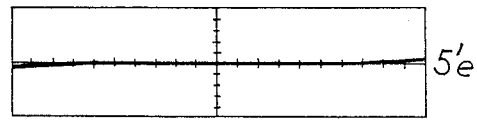
Figure 5:
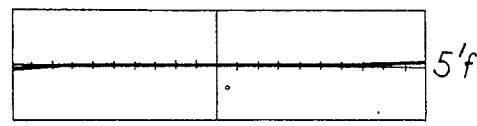

For FIGS. 5 and 5' the light beam is in the sagittal plane, perpendicular to the plane of the figure.

In the diagrams shown in these figures the scale for the horizontal axis is always the same, the radius of the entry pupil of the system being assumed to correspond to one unit of this scale.

|  | RADIUS (mm) | AXIAL DISTANCE (mm) | REFRACTIVE INDEX | CONIC CONSTANT |
| --- | --- | --- | --- | --- |
| ophthalmic lens 10 | $R_1 = 18.155$ | $D_1 = 10$ | $n_l =$ | $K_1 =$ |
|  | $R_2 = 400.000$ |  | 1.52300 | $-0.185790$ |
| air |  | $D_2 = 13$ |  |  |
| cornea 13 | $R_3 = 7.720$ | $D_3 =$ | $n_3 =$ | $K_3 =$ |
|  | $R_4 = 6.500$ | 0.550 | 1.36700 | $-0.26000$ |
| aqueous humour |  | $D_4 =$ 2.000 | $n_4 =$ 1.33740 |  |
| intra-ocular lens 11 | $R_5 = -6.200$ | $D_5 =$ | $n_5 =$ | $K_5 =$ |
|  | $R_6 = 6.200$ | 0.500 | 1.49200 | $-2.699500$ |
| aqueous humour |  | $D_6 =$ 0.550 | $n_4 =$ 1.33740 |  |
| iris 14 | $\infty$ |  |  |  |
| aqueous humour |  | $D_7 =$ 2.000 | $n_4 =$ 1.33740 |  |
| sac 15 | $\infty$ |  |  |  |
| vitreous humour |  | $D_8 =$ 18.341 | $n_6 =$ 1.33600 |  |
| retina 17 | $R_7 = -12.000$ |  |  |  |

In FIGS. 4 and 5 the scale on the vertical axis is assumed to correspond to a maximum value equal to 0.005 mm.

In FIGS. 4' and 5', however, it is assumed to correspond to a maximum value equal to 0.1 mm.

In diagrams 4a and 4'a the point source is on the axis of the system.

In the other diagrams it is offset from this axis, by 5 mm for diagrams 4b and 5b, by 10 mm for diagrams 4c and 5c, by 20 mm for diagrams 4'd and 5'd, by 40 mm for diagrams 4'e and 5'e and by 60 mm for diagrams 4'f and 5'f.

Those skilled in the art will see from these diagrams that the optical system having the numerical values set out in the table above is substantially aplanatic for a $2 \times 10$ mm diameter object field, the longitudinal spherical aberration of the system that it forms with the eye 12 concerned and the coma being sustantially zero for this field.

For this $2 \times 10$ mm diameter field the image of a point source is in practise a spot with a diameter equal to five microns, which corresponds to the diameter of the retinal detectors.

The diagrams in FIGS. 4, 4', 5 and 5' also show that the aberration curves are virtually flat for an object field from $2 \times 20$ mm through $2 \times 60$ mm.

There is no more spherical longitudinal aberration and there remains only very slight coma, especially for a $2 \times 60$ mm diameter object field.

For the most part the aberration caused by an optical system of this kind is astigmatic, which can be tolerated.

In all cases the longitudinal spherical aberration remains very much less than that of an emmetropic eye under the same conditions. Of course, the present invention is not limited to the embodiment described and shown but encompasses any variant execution thereof. In particular, both surfaces of at least one of the lenses used may be aspherical.

I claim:

1. Optical system for improving the sight of a person suffering from macular degeneration comprising a high positive power ophthalmic lens adapted to be disposed in front of the eye to be treated and a high negative power intra-ocular lens adapted to be implanted in the eye to be treated after removal of its crystalline lens, wherein at least one surface of each lens is an aspherical surface of revolution, and the aspherical surface of revolution of each lens having a generatrix that is a conic section.

2. System according to claim 1 wherein said aspherical surface of revolution of both lenses has a generatrix that is an ellipse.

3. System according to claim 2 wherein for an overall power of said intra-ocular lens of −50 diopters the conic constant is between −0.1 and −0.3 for an ophthalmic lens with a refractive index equal to 1.523 and between −2 and −4 for an intra-ocular lens with a refractive index equal to 1.492.

4. System according to claim 3 wherein said conic constant is equal to −0.185790 for said ophthalmic lens and is equal to −2.699500 for said intra-ocular lens.

5. System according to claim 4 wherein said surface of one of said lenses which is an aspherical surface of revolution is its front surface.

6. Optical system according to claim 5 wherein said intra-ocular lens comprises an anterior chamber intra-ocular lens configured for implanatation in the anterior chamber of the eye to be treated.

7. System according to claim 2 wherein the longitudinal spherical aberration of the system that it forms with the eye concerned is less than that of an emmetropic eye under the same conditions.

8. System according to claim 7 which is substantially aplanatic for a 2×10 mm diameter object field.

* * * * *